United States Patent [19]

Bienkowski

[11] Patent Number: 4,622,844
[45] Date of Patent: Nov. 18, 1986

[54] OXYGEN SENSOR MONITOR

[75] Inventor: Joseph V. Bienkowski, Fostoria, Ohio

[73] Assignee: Allied Corporation, Morristown, N.J.

[21] Appl. No.: 725,857

[22] Filed: Apr. 22, 1985

[51] Int. Cl.[4] .............................................. G01D 18/00
[52] U.S. Cl. ..................................... 73/1 G; 204/401
[58] Field of Search ...................... 73/1 G, 23, 27 R; 204/401, 1 Y, 1 T

[56] References Cited

U.S. PATENT DOCUMENTS

| 4,094,186 | 6/1978 | Wessel | 73/1 G |
| 4,223,549 | 9/1980 | Kitzinger | 73/1 G X |
| 4,335,369 | 6/1982 | Taniguchi et al. | 338/34 |
| 4,348,732 | 9/1982 | Kreft | 73/1 G X |
| 4,389,881 | 6/1983 | Butler et al. | 73/1 G X |
| 4,494,399 | 1/1985 | Youngman | 73/1 G |

FOREIGN PATENT DOCUMENTS

| 1523027 | 4/1969 | Fed. Rep. of Germany | 73/1 G |
| 5789 | 1/1979 | Japan | 73/1 G |
| 163862 | 10/1982 | Japan | 73/1 G |
| 163863 | 10/1982 | Japan | 73/1 G |
| 42963 | 3/1983 | Japan | 73/1 G |
| 645023 | 1/1979 | U.S.S.R. | 73/1 G |

Primary Examiner—Michael J. Tokar
Assistant Examiner—Tom Noland
Attorney, Agent, or Firm—Leo H. McCormick, Jr.; Ken C. Decker

[57] ABSTRACT

A monitor (26) for use in a vehicle to check the operation of an oxygen sensor (20). The monitor (26) has a regulator (64) that changes the fluctuating voltage associated with a vehicle electrical system into a stable voltage source. An amplifier (68) receives an output signal from the oxygen sensor (20) and generates a buffered output signal. A comparator (70) compares the buffered output signal with a reference signal. When the buffered output signal is equal to the reference signal, the source voltage from the regulator (64) activates a diode (40) to inform an operator that the output voltage of the oxygen sensor (20) is within acceptable operating limits.

2 Claims, 3 Drawing Figures

OXYGEN SENSOR MONITOR

BACKGROUND OF THE INVENTION

This invention relates to a monitor for use in a vehicle to check the operation of an oxygen sensor.

Three-way catalytic converters used on automotive engines are the most commonly used method for meeting the emissions requirements established by the regulations set forth in the Clean Air Act of Dec. 31, 1970 in the U.S. When a closed loop system having a catalytic converter is used, an oxygen sensor is located in the exhaust manifold to provide a feedback signal to an electronic control unit. The electronic control unit maintains the engine input air to fuel ratio as near stoichiometry as possible for peak catalytic converter efficiency by measuring the oxygen type content in the exhaust gas. Both galvanic oxygen sensor (zirconia) of the type disclosed in U.S. Pat. Nos. 3,835,012, 4,107,018, 4,147,513, 4,377,801 and 4,387,359 and resistive (titania) oxygen sensors of the type disclosed in U.S. Pat. No. 4,007,435 have been evaluated as a way to measure the oxygen content in an exhaust gas.

In all of the prior art sensors some efforts have been made to reduce the effect of exhaust gas on the sensor element, such as by applying a coating on the sensor element or providing baffles in order to prevent the direct contact of the exhaust gas with the sensor element. However, after an extended period of use, particles of materials carried by the exhaust gas can be deposited on the sensor element and/or a chemical reaction may occur with the exhaust gases that can result in the generation of incorrect feedback signals.

It is anticipated that in the future it may be necessary to check the operation of the oxygen sensors as part of good maintenance practices as often as every ten thousand (10,000) miles.

SUMMARY OF THE INVENTION

The monitor disclosed herein is designed to be portable and used on many vehicles for checking the functional operation of an oxygen sensor. The monitor is connected to receive the feedback signal from the oxygen sensor in the vehicle. A buffer amplifier receives the feedback signal and generates a corresponding operational signal when connected to a source of electrical voltage. The operational signal is transmitted to a comparator and compared with a reference signal to develop an indicator signal. The indicator signal is transmitted to a visual display to inform an operator of the functioning of the oxygen sensor.

An advantage of this monitor occurs through its mobility and simplicity since the visual display informs an operator if an oxygen sensor is functioning within set limits.

It is an object of this invention to provide an oxygen sensor system with a monitor to check the functioning of an oxygen sensor element.

It is a further object of this invention to provide a portable monitor through which the functioning of an oxygen sensor can be checked.

BRIEF DESCRIPTION OF THE INVENTION

The invention will now be disclosed with reference to the accompanying drawings wherein:

FIG. 1 is a schematic illustration of an automobile engine having an oxygen sensor therein with a monitor made according to the invention disclosed herein connected thereto to check the functioning thereof; and FIG. 2 is a pictorial illustration of the monitor of FIG. 1; and FIG. 3 is a schematic illustration of the electrical circuit of the monitor of FIG. 2.

DETAILED DESCRIPTION OF THE INVENTION

Figure 1:
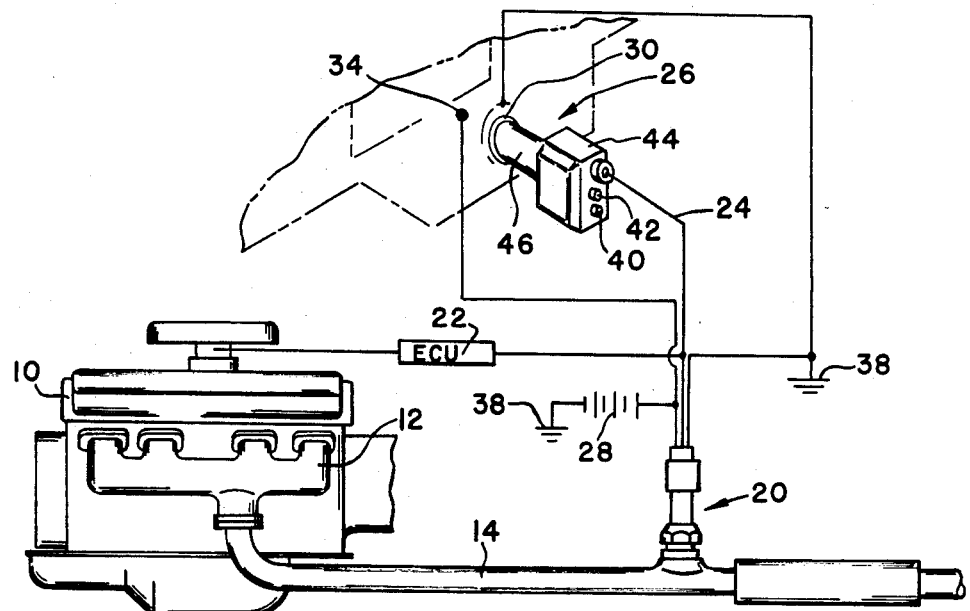

In FIG. 1, a reciprocating type internal combustion engine 10 is shown with an exhaust manifold 12 connected to a pipe 14 which carries exhaust gas to the surrounding environment. An oxygen sensor 20 located in pipe 14 detects the oxygen content in the exhaust gas and supplies an electronic control unit 22 with an input signal. The electronic control unit 22 reacts to the input signal by controlling the air to fuel ratio supplied to operate engine 10. The correct air to fuel ratio helps to maintain the exhaust gas within the emission standards set by the clean air regulations for the U.S. If for some reason the input signal supplied to the electronic control unit 22 is incorrect, the air to fuel ratio is correspondingly affected.

In order to check the operation of the oxygen sensor 20, a lead 24 is connected to receive the input signal that is currently supplied to the electronic control unit 22. The lead 24 is connected to monitor 26. The monitor 26 is connected to the power supply 28 of the vehicle through any convenient connection such as the cigarette lighter 30. When the end 33 of probe 32 on monitor 26 engages contact 34 and probe 36 is connected to an electrical ground 38, a power indicator 40 (a light or diode) is turned on to inform an operator that electrical voltage is being supplied to the monitor 26. With the engine 10 running, the input signal from the oxygen sensor 20 is being evaluated by the monitor 26 to make sure that the input signal is within the operating standards. If the input signal is greater than 0.45 v (rich condition), an operational indicator 42 is turned on to inform the operator that the oxygen sensor 20 is exposed to a rich exhaust gas condition.

Figure 2:
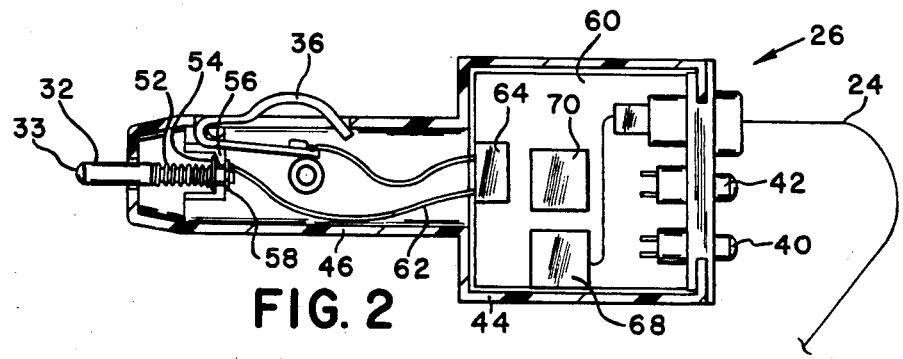
Figure 3:
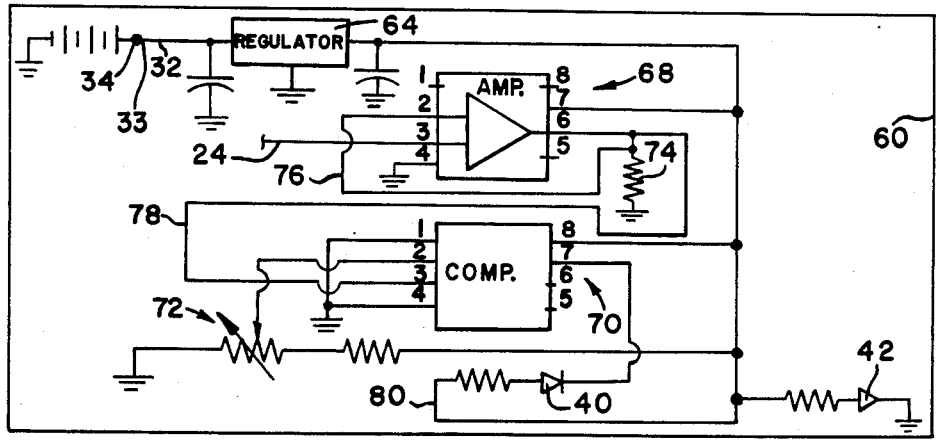

The monitor 26 is shown in more particular detail in FIGS. 2 and 3. FIG. 2 is an illustration of the components of the monitor 26 and FIG. 3 is a schematic of the electrical circuit therein.

In FIG. 2 a nonelectrically conductive housing 44 has a cylindrical section 46 that extends from a rectangular section 44. Probe 32, which is located in the cylindrical section 46 has a spring 52 attached thereto. A ring 54 located on the probe 32 is positioned on one side of a wall 56. Spring 52 acts on the probe 32 to bring end 58 thereon into engagement with wall 56. On insertion of the cylindrical section into the cigarette lighter 30, probe end 33 engages the contact 34 to supply circuit board 60 with an electrical voltage. Spring 52 continually urges end 33 toward contact 34 to assure that a good electrical connection is achieved. At the same time, probe 36 engages the sides of the cigarette lighter 30 to connect ground 38 with circuit board 60.

The electrical voltage transmitted through probe 32 is carried on lead 62 to a voltage regulator 64. The voltage regulator 64 changes the fluctuating battery voltages into a stable voltage. While any stable voltage could be chosen, a voltage regulator manufactured by Motorola and sold under the trade designation of 78L08 was selected in order to provide a stable voltage of 8 volts in lead 66.

The 8 volts in lead 66 is simultaneously supplied to a buffer amplifer 68, a comparator 70, a variable resistor 72, a first diode 40 and a second diode 42.

The output voltage in lead 66 is carried through a resistor into diode 42. When diode 42 is lit (or on) the operator knows voltage is being supplied to monitor 26.

The buffer amplifier 68 is an eight pin chip sold by RCA under the trade designation CA3140E. As shown in FIG. 3, the input signal from the oxygen sensor 20 is connected by lead 24 to pin #3. Pin #2 is connected by lead 76 to resistor 74 and then to ground 38. Pin #6 is connected to lead 76 and lead 78 to pin #3 in comparator 70. Pin #7 is connected to receive the stable 8 volts from lead 66. The buffer amplifier 68 generates an output signal that corresponds to the output signal of the oxygen sensor 20 without applying a significant load on the sensor 20. The buffered output signal is transmitted on lead 78 to comparator 70.

The comparator 70 is an eight pin chip sold by Motarola under the trade designation of LM311N. As shown in FIG. 3, pin #2 is connected to a variable resistor 72. The variable resistor 72 is connected through a fixed resistor 71 to receive the fixed voltage from lead 66. By adjusting the variable resistor, a set reference signal is provided for the comparator 70. Pin #3 receives the buffered output signal from amplifier 68. The stable voltage from lead 66 is connected to pin #8. Pin #7 carries the output of the comparator 70 to diode 40. The comparator 70 compares the buffered output signal with the reference signal. When the reference input voltage is equal to the buffered output signal, which for this application is 0.43 volts, the output from pin #7 is essentially zero and acts as a ground so that the stable voltage supplied by lead 80 to diode 40 allow the diode 40 to be activated. With diode 40 activated, the operator is informed that the output signal of the oxygen sensor 20 is indicative of a rich contition.

When the output from comparator 70 as supplied to diode 40 is such that a ground is not created, diode 40 remains off and thus the operator is informed that the corresponding output signal from oxygen sensor 20 is indicative of a lean contition. Normal closed-loop operation of the entire vehicle/engine is indicated by the flashing of diode 40 at a low repetition rate (1–4 Hz).

I claim:

1. A portable monitor for use in a vehicle to check the operation of an oxygen sensor comprising:
   a housing having a rectangular body with a projection extending therefrom, said projection having a wall with a slot therein;
   a first probe having a first end that extends through said projection and a second end that extends through said wall;
   a spring connected to said wall for urging said second end of probe toward said wall;
   a second probe having a portion that extends through said projection;
   a receptacle connected to a source of electrical voltage and an electrical ground, said projection being connected to said receptacle, said spring urging said first probe into electrical contact with said electrical voltage and said second probe engaging said receptacle and thereby being connected to said electrical ground;
   regulator means located in said rectangular body connected to said source of electrical voltage to establish a stable source of electrical voltage;
   a first indicator light connected to said regulator means and electrical ground through said second probe for informing an operator of the availability of stable electrical voltage;
   buffer means connected to said regulator, electrical ground and oxygen sensor for generating an output signal corresponding to an operational signal developed in said oxygen sensor;
   means for comparing said output signal with a reference signal to develop an indicator signal; and
   a second indicator light connected to said regulator and responsive to said indicator signal for providing an operator with an indication of the functioning of said oxygen sensor.

2. The monitor, as recited in claim 1 further including:
   means for adjusting said reference signal to correspondingly change said indicator signal.

* * * * *